(12) United States Patent
Chance et al.

(10) Patent No.: US 10,765,864 B2
(45) Date of Patent: Sep. 8, 2020

(54) RETINAL-INSPIRED METHOD AND SYSTEM FOR IMPROVED DETECTION

(71) Applicant: National Technology & Engineering Solutions of Sandia, LLC, Albuquerque, NM (US)

(72) Inventors: Frances S. Chance, Albuquerque, NM (US); Christina E. Warrender, New Ipswich, NH (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 111 days.

(21) Appl. No.: 16/059,746

(22) Filed: Aug. 9, 2018

(65) Prior Publication Data

US 2020/0046979 A1 Feb. 13, 2020

(51) Int. Cl.
| | |
|---|---|
| *A61N 1/36* | (2006.01) |
| *G06K 9/60* | (2006.01) |
| *G06N 3/04* | (2006.01) |
| *A61F 2/14* | (2006.01) |

(52) U.S. Cl.
CPC ............ *A61N 1/36046* (2013.01); *A61F 2/14* (2013.01); *G06K 9/605* (2013.01); *G06N 3/049* (2013.01)

(58) Field of Classification Search
CPC ...... A61N 1/36046; G06N 3/049; A61F 2/14; G06K 9/605
See application file for complete search history.

(56) References Cited

U.S. PATENT DOCUMENTS

| | | | |
|---|---|---|---|
| 9,294,690 B1* | 3/2016 | Caulfield | H04N 5/33 |
| 2014/0016871 A1* | 1/2014 | Son | G06K 9/46 |
| | | | 382/201 |
| 2015/0310303 A1* | 10/2015 | Andreopoulos | G06K 9/4676 |
| | | | 382/158 |
| 2018/0173992 A1* | 6/2018 | Zink | G06T 1/20 |
| 2019/0244078 A1* | 8/2019 | Franca-Neto | G06K 9/6271 |
| 2019/0332929 A1* | 10/2019 | Schie | G06N 3/0635 |

OTHER PUBLICATIONS

Bagheri et al., "Performance of an insect-inspired target tracker in natural conditions," Bioinspiration & Biomimetics, vol. 12, No. 2, published Feb. 16, 2017, 16 pages.

* cited by examiner

*Primary Examiner* — Nizar N Sivji
(74) *Attorney, Agent, or Firm* — Yee & Associates, P.C.

(57) ABSTRACT

The present disclosure provides a method and device for filtering sensor data. Signals from an array of sensor pixels are received and checked for changes in pixel values. Motion is detected based on the changes in pixel values, and motion output signals are transmitted to a processing station. If the sum of correlated changes in pixel values across a predetermined field of view exceeds a predetermined value, indicating sensor jitter, the motion output signals are suppressed. If a sum of motion values within a defined subsection of the field of view exceeds a predetermined threshold, indicating the presence of a large object of no interest, the motion output signals are suppressed for that subsection.

20 Claims, 8 Drawing Sheets

PIXEL ARRAY

| PIXEL (1,1): DETECTS AND TRANSMITS VALUE OF SIGNAL AT LOCATION (1,1) | PIXEL (2,1) | PIXEL (3,1) | PIXEL (4,1) | o o o |
|---|---|---|---|---|
| PIXEL (1,2) | PIXEL (2,2) | PIXEL (3,2) | PIXEL (4,2) | o o o |
| PIXEL (1,3) | PIXEL (2,3) | PIXEL (3,3) | PIXEL (4,3) | o o o |
| PIXEL (1,4) | PIXEL (2,4) | PIXEL (3,4) | PIXEL (4,4) | o o o |
| o o o | o o o | o o o | o o o | |

FIG. 4

LAYER B - EXAMPLE

| $B(1,1)=[P(1,1,t) -P(1,1,t-\Delta t)]_+$ | B(2,1) | B(3,1) | B(4,1) | ∘ ∘ ∘ |
|---|---|---|---|---|
| B(1,2) | B(2,2) | B(3,2) | B(4,2) | ∘ ∘ ∘ |
| B(1,3) | B(2,3) | B(3,3) | B(4,3) | ∘ ∘ ∘ |
| B(1,4) | B(2,4) | B(3,4) | B(4,4) | ∘ ∘ ∘ |

LAYER L - EXAMPLE

| G(1,1) | G(2,1) | G(3,1) | G(4,1) | G(5,1) |
|---|---|---|---|---|
| G(1,2) | G(2,2) | G(3,2) | G(4,2) | G(5,2) |
| G(1,3) | G(2,3) | G(3,3) | G(4,3) | G(5,3) |
| G(1,4) | G(2,4) | G(3,4) | G(4,4) | G(5,4) |
| G(1,5) | G(2,5) | G(3,5) | G(4,5) | G(5,5) |

FIG. 11

RETINAL-INSPIRED METHOD AND SYSTEM FOR IMPROVED DETECTION

STATEMENT OF GOVERNMENT INTEREST

This invention was made with United States Government support under Contract No. DE-NA0003525 between National Technology & Engineering Solutions of Sandia, LLC and the United States Department of Energy. The United States Government has certain rights in this invention.

BACKGROUND INFORMATION

1. Field

The present disclosure relates generally to sensors systems and more specifically to processing sensor data using retinal model neuromorphic sensor platforms.

2. Background

A major challenge facing detection systems is detecting signals-of-interest against various forms of clutter or distractor signals. The difficulty of this task is amplified by advances in sensor sensitivity and additions of multiple sensor modalities into the detection system. Modern detection systems must therefore have the capability to handle an ever-increasing diversity of clutter. Particularly challenging is detecting moving objects that are both small and relatively low-contrast (dim).

While techniques exist that can filter these types of clutter, they are insufficient because they require computational resources that are incompatible with size, weight, and power (SWAP) constraints of sensor platforms.

Inspiration for handling this clutter can be drawn from biological visual systems. The retina plays an important role in animal vision—namely preprocessing visual information before sending it to the brain through the optic nerve. Understanding how the retina does this is of particular relevance for development and design of neuromorphic sensors, especially those focused towards image processing.

However, while retinal circuitry may appear simple compared to higher-level areas of the brain such as the cortex, the retina plays a crucial role in processing sensory information. Because the bandwidth of the optic nerve is limited, it is widely assumed that the retina compresses visual information by discarding irrelevant or redundant information. The retina contains a surprising diversity of retinal ganglion types that perform an equally wide range of computations (detecting motion, color, etc.) to "preprocess" visual input for transmission through the information bottleneck of the optic nerve.

Moreover, recent development of neuromorphic hardware and architectures with demonstrated energy-savings and performance efficiency highlight a clear opportunity to implement neuromorphic systems on sensor platforms. In neuromorphic computing, also known as neuromorphic engineering, very-large-scale integration (VLSI) systems containing electronic analog circuits are used to mimic neuro-biological architectures present in the nervous system. Neuromorphic systems may include analog, digital, mixed-mode analog and digital VLSI, and software systems that implement models of neural systems. Neuromorphic computing may be implemented on the hardware level using oxide-based memristors, threshold switches, and transistors.

Therefore, it may be desirable to provide a method and system that mimics the retinal model to preprocess sensor information in order to free up bandwidth for transmitting signals of interest.

SUMMARY

An embodiment of the present disclosure provides a sensor data filtering device, comprising a first layer configured to receive signals from an array of sensor pixels and determine changes in pixel values. A second layer is configured to receive the changes in pixel values from the first layer, detect motion based on the changes in pixel values and transmit motion output signals to a processing station. A third layer is configured to receive the changes in pixel values from the first layer and detect correlated changes in pixel values across a predetermined field of view, wherein the third layer is configured to modify the motion output signals of the second layer if a sum of correlated changes in pixel values within the field of view exceeds a predetermined threshold. A fourth layer is configured to receive motion output signals from the second layer and integrate motion values within defined subsections of the field of view, wherein the fourth layer is configured to modify the motion output signals of the second layer for a subsection if a sum of motion values within that subsection exceeds a predetermined threshold.

Another embodiment of the present disclosure provides a method of filtering sensor data, comprising the steps of receiving signals from an array of sensor pixels and determining changes in pixel values; detecting motion based on the changes in pixel values and transmitting motion output signals to a processing station; detecting correlated changes in pixel values across a predetermined field of view and modifying the motion output signals if a sum of correlated changes in pixel values within the field of view exceeds a predetermined threshold; and integrating motion values within defined subsections of the field of view and modifying the motion output signals of the second layer for a subsection if a sum of motion values within that subsection exceeds a predetermined threshold.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 4 is an illustration of an example pixel array in accordance with the illustrative embodiment;

FIG. 11 depicts an example application of size tuning to an array of motion detection units in Layer G in accordance with an illustrative embodiment.

DETAILED DESCRIPTION

Illustrative embodiments recognize and take into account that the computational capabilities of biological systems have garnered interest within the research community seeking to develop new methods of high-speed, low-power computing. Numerous novel hardware systems have been built to instantiate neuromorphic computing principles and to solve challenging problems such as pattern recognition.

Illustrative embodiments provide a method and system inspired by the retina that filters clutter at the sensor level. This produces the technical effect of freeing up bandwidth for transmitting and processing signals of interest. The illustrative embodiments address white noise as might arise as a result of thermal noise within the sensor. The illustrative embodiments also deal with correlated changes across the entire field of view of the sensor resulting from sensor jitter, as well as correlated changes within a spatial area such as those produced by relatively large objects, e.g., buildings, that might not be of interest.

Illustrative embodiments are applicable to image processing for remote sensing, streaming video or autonomous platforms, and security systems with significant size, weight, and power (SWAP) constraints. Illustrative embodiments can be applied on existing hardware platforms and are also applicable to emerging neuromorphic architectures as low-power alternatives to existing hardware platforms.

Figure 1:
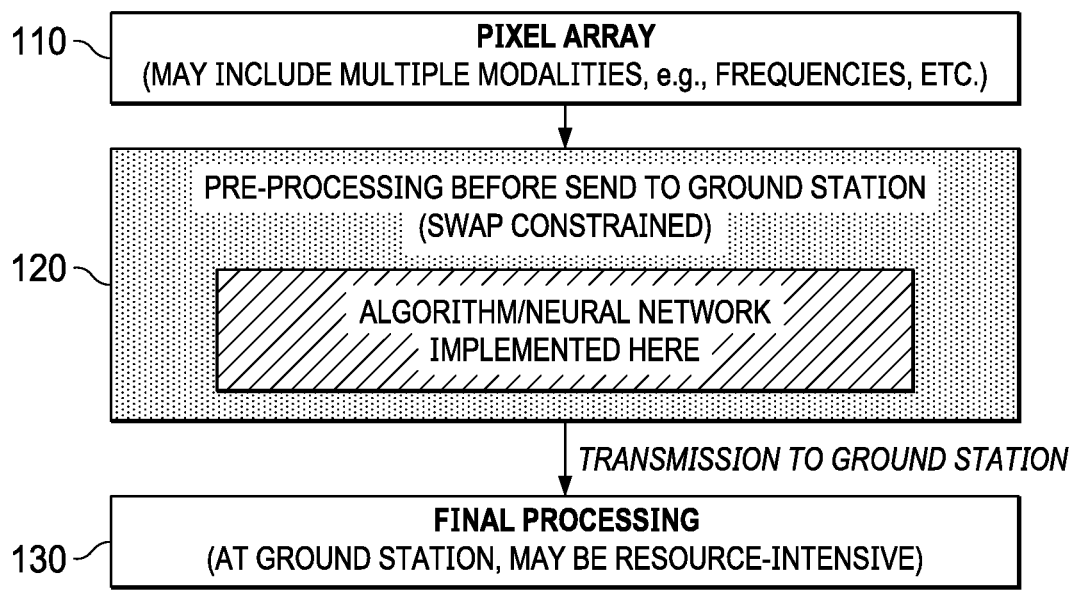
FIG. 1 is a process flow for a remote processing pipeline in accordance with an illustrative embodiment.

Referring now to FIG. 1, a process flow for a remote processing pipeline is illustrated in accordance with an illustrative embodiment. In this embodiment a remote sensor comprises a pixel array 110 that may encompass multiple modalities, e.g., visual light, infrared (IR), ultraviolet (UV), synthetic aperture radar (SAR) data, etc. The sensor may be mounted on any number of remote sensing platforms including, for example, cameras, unmanned aerial vehicles (UAV), telescopes, satellites, etc.

Such sensing platforms typically have to operate under strict SWAP constraints, requiring a remote processor at a ground station to process the sensor data. This final processing at the ground station can be very resource intensive and considerable bandwidth may be required to transmit the raw sensor data from the sensor platform to the ground station or control station.

The present disclosure incorporates a preprocessing algorithm and hardware 120 between the sensor pixel array 110 and the final processing 130. This preprocessing 120 occurs at the sensor platform and filters the raw sensor data for signals of interest before sending the data to the ground station. This preprocessing reduces overall bandwidth and processing requirements at the ground station while also respecting the SWAP constraints of the sensor platform.

Figure 2:
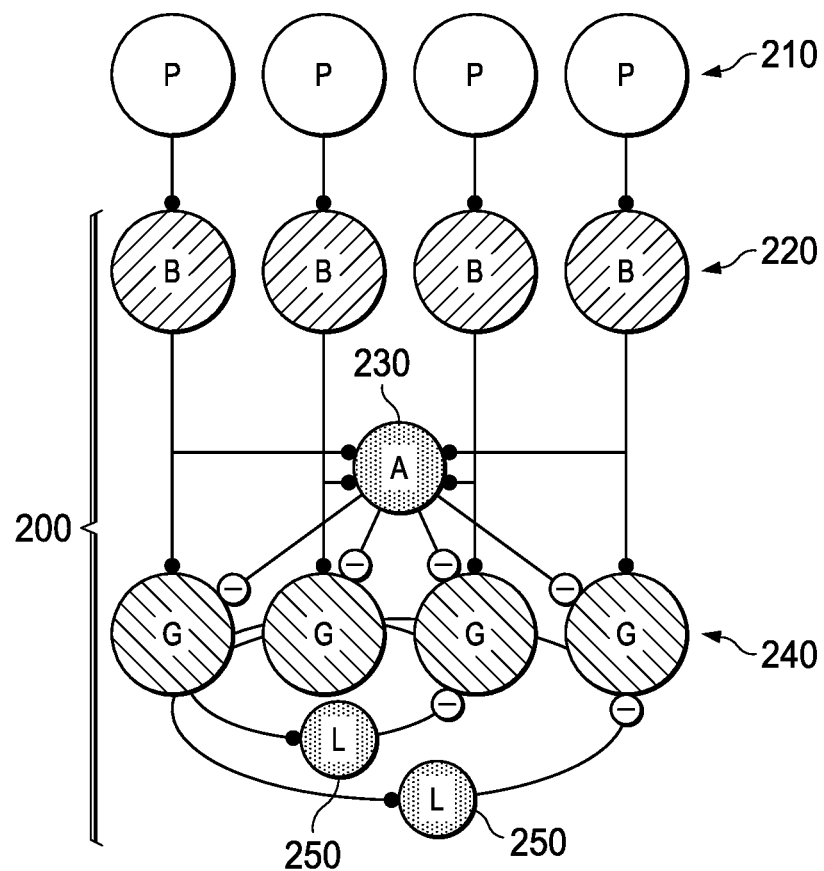
FIG. 2 depicts a preprocessing architecture incorporated into a sensor platform in accordance with an illustrative embodiment.
Figure 3:
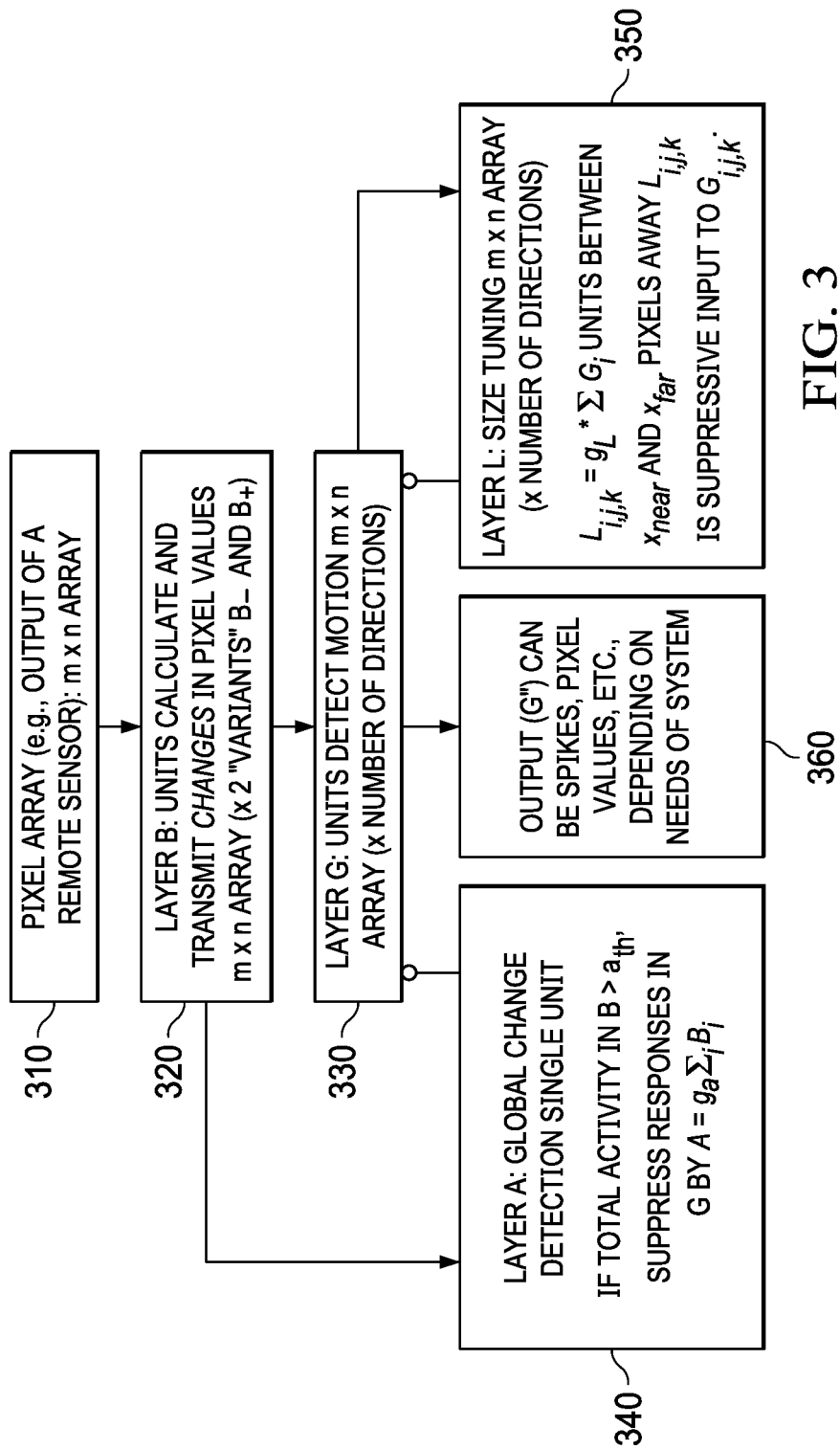
FIG. 3 is a flowchart depicting the operation of the preprocessing components in accordance with an illustrative embodiment.

FIG. 2 depicts a preprocessing architecture incorporated into a sensor platform in accordance with an illustrative embodiment. The preprocessing device 200 comprises four layers. FIG. 3 is a flowchart depicting the operation of the preprocessing components in accordance with the illustrative embodiment.

The sensor comprises an m×n array 210 of pixels P. An example pixel array is depicted in FIG. 4 in accordance with the illustrative embodiment. The output of the pixel array 210 is the input to the preprocessing device 200 (step 310). In the example depicted in FIG. 4, the array is a two dimensional (2-D) pixel array such as in a camera mounted on a UAV or satellite. Each pixel, e.g., Pixel (1,1), detects and transmits the value of a signal at its respective location.

Detectors in Layer B 220 receive the signals from the respective sensor pixels and process and transmit changes in pixel values (step 320). These pixel value changes are sent directly to Layer A 230 and Layer G 240.

The detectors in Layer G 240 detect local motion between two pixels which might represent, for example a moving object against a background (step 330).

To improve the accuracy of the motion detection and reduce extraneous signals such as background clutter and sensor jitter, the output of Layer G 230 is tuned by the remaining two layers of the device to account for both global motion and lateral interaction (object size).

The tunable global unit in Layer A 230 receives pixel value changes from several detectors in layer 220. Layer A 230 detects correlated change in pixel values across a predetermined field of view of the sensor. If the total correlated change transmitted by Layer B 220 exceeds a predetermined threshold, Layer A 230 suppresses motion signals generated by the units in Layer G 240 (step 340). Such highly correlated global motion of objects across the field of view (whether foreground or background) is an indication that it was in fact the sensor that moved (jitter) rather than an object within the field of view. Therefore, there is no need to transmit signals representing such clutter, thereby saving transmission bandwidth and processing resources.

In addition to global tuning, the device also provides size tuning of motion signals to take account of large environmental objects within the field of view that may be moving slowly or appear to be moving as a result of changing angles of view caused by the movement of the sensor platform. Examples of such large objects include clouds, contours of bodies of water, buildings, and other large stationary objects. "Distractors" arising from these types of larger objects, due to their size, are known to be uninteresting. Therefore, once such objects are identified within the field of view any motion signals associated with them are not of interest and can be filtered to save bandwidth and processing.

The units in Layer L 250 provide this type of size tuning of motion signals generated by Layer G 240. These units integrate detected motion over smaller subsections of the field of view and tune the G units for targets of specific sizes. The field of view subsections are defined by a specified distance between pixels. If the sum of motion signals within such a subsection exceeds a specified threshold, the units in Layer L 250 suppress the transmission of these signals by the respective units in Layer G 240 (step 350).

Whereas global tuning assumes that highly correlated pixel value changes across the whole field of view are produced by the sensor motion rather than moving objects, size tuning assumes that highly correlated motion signals within a subsection of the field of view are most likely due to an object but one that is too big to be of interest and can thereby be filtered from transmission to the ground station or control station.

The output G" of level 240, tuned for global movement and object size, is sent to the ground station or control station for further processing (step 360). G" consists of events or tiles of data denoted by events. Depending on the specific needs of the system in question, the output may take various forms. For example, the output may be in the form of signal spikes, in other cases the outputs might be values of information recorded at specific locations, e.g., pixel values recorded by a camera at detected locations.

Figures 5, 6:
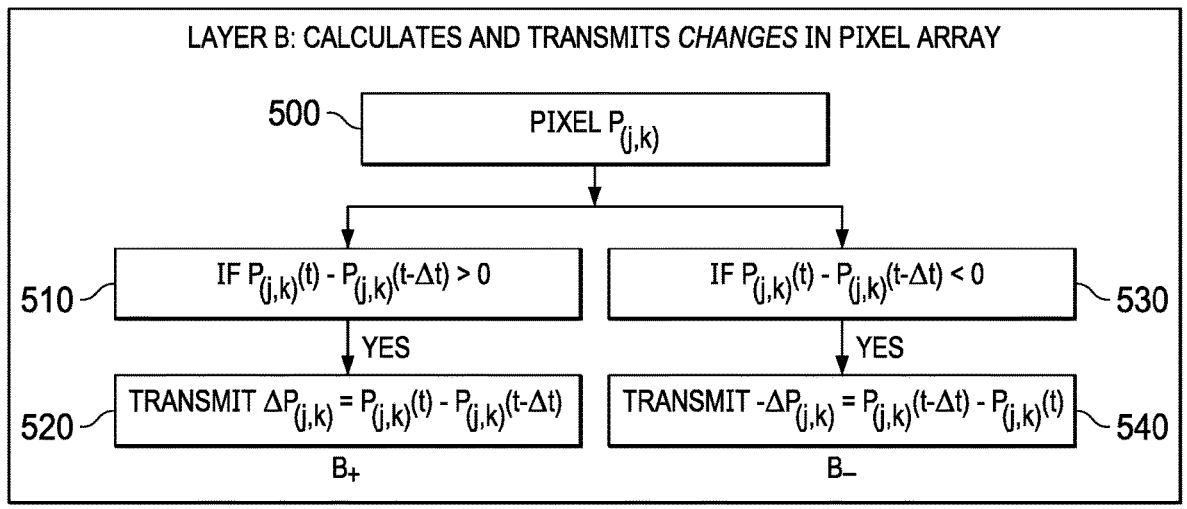
FIG. 5 depicts a detailed process flow showing the operation of Layer B calculating and transmitting pixel value changes in accordance with an illustrative embodiment.
FIG. 6 is a representation of a detector array in Layer B in accordance with an illustrative example.

FIG. 5 depicts a detailed process flow showing the operation of Layer B calculating and transmitting pixel value changes in accordance with an illustrative embodiment. FIG. 6 is a representation of a detector array in Layer B in accordance with the illustrative example. Layer B is an m×n layer (the same dimensions as pixel layer). Each unit calculates the change in signal (P(t)−P(t−Δt), where Δt is the value of pixel P at some unit of time before.

In the example illustrated in FIG. 6, only positive changes (i.e. increases in luminance) are transmitted. Variations include:

1) transmitting only positive changes, $B_+$, as illustrated above, $\lfloor \ \rfloor_+$ indicates rectification
$\lfloor x \rfloor_+ =$ if $x \geq 0$
$\lfloor x \rfloor_+ = 0$ if $x<0$ 2) transmitting only negative changes, $B_-$ (e.g. $B_-(1,1) = \lfloor P(1,1,t-\Delta t)-P(1,1,t) \rfloor_+)$ 3) transmitting both positive and negative changes ($B_+$ and $B_-$) via two parallel pathways.

The example process flow depicted in FIG. 5 illustrates transmitting both positive and negative changes in pixel values. For a given pixel $P_{(j,k)}$ 500, if the difference in values between time (t) and time (t−Δt) is greater than zero (>0) (step 510), this positive difference in pixel value $\Delta P_{(j,k)}$ is transmitted to Layer G as $B_+$ (step 520).

Likewise, if the difference in values between time (t) and time (t−Δt) is less than zero (<0) (step 530), this negative difference in pixel value $-\Delta P_{(j,k)}$ is transmitted to Layer G as $B_-$ (step 540).

Figure 7:
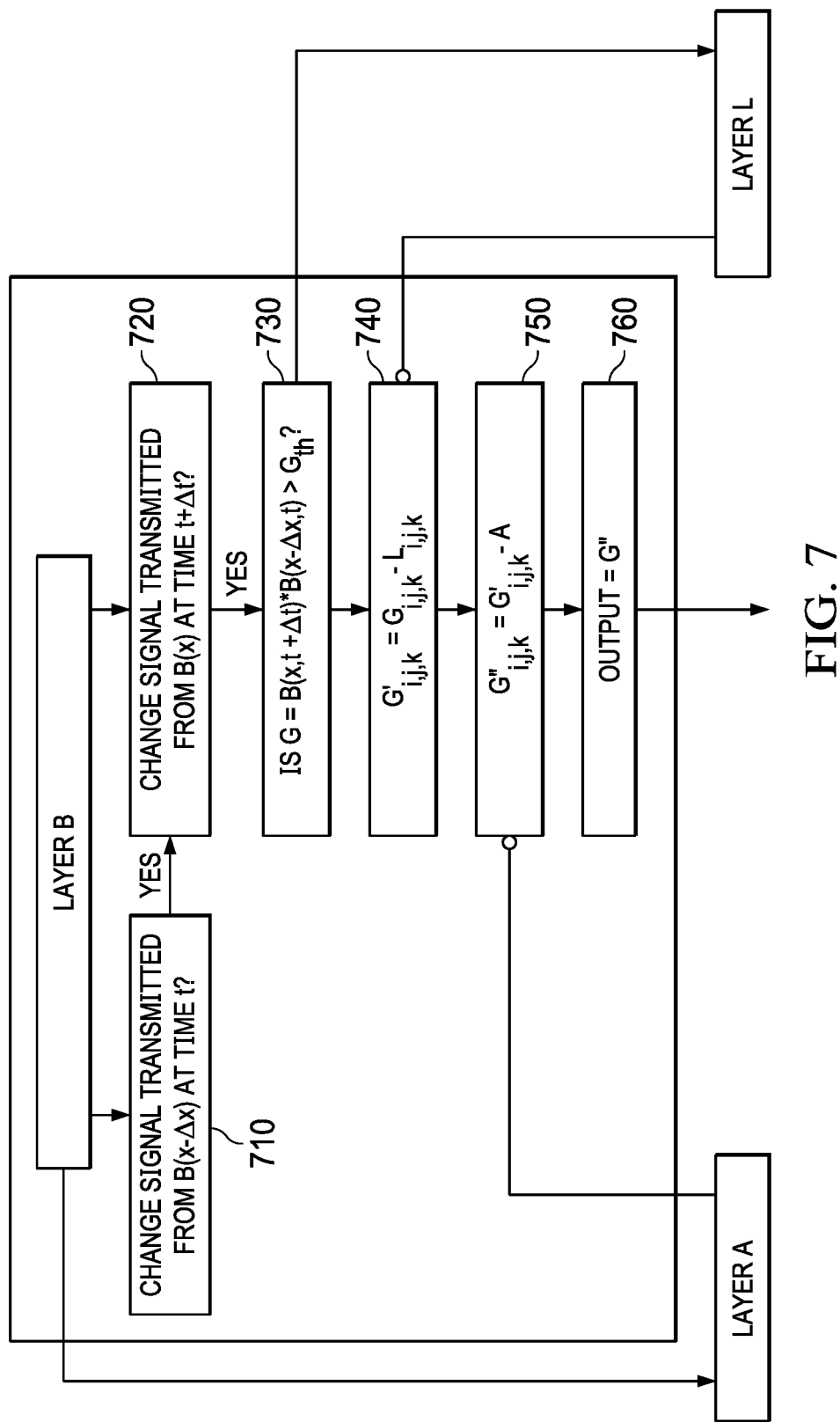
FIG. 7 depicts a detailed process flow showing the operation of Layer G calculating and transmitting motion output signals in accordance with an illustrative embodiment.
Figure 8:
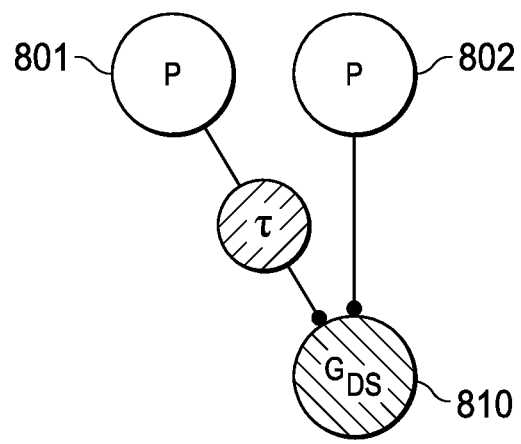
FIG. 8 depicts the transmission of spatially and temporally offset information from pixels to direction-selective units in Layer G in accordance with an illustrative embodiment.

FIG. 7 depicts a detailed process flow showing the operation of Layer G calculating and transmitting motion output signals in accordance with an illustrative embodiment. Similar to Layer B, Layer G comprises an m×n array of units to match the dimensions of the pixel layer. The units in Layer G are direction selective and receive spatially and temporally offset information from the pixels (via Layer B). This spatial and temporal offset is illustrated in FIG. 8, represented by τ. Because pixel 801 is laterally offset from direction-selective unit 810, its signal will take longer to reach unit 810 than the signal from pixel 802.

Returning to FIG. 7, for a given position x (Pixel(j,k)) the determination is made whether there is a change signal transmitted from unit B(x−Δx) in Layer B at time t (step 710), where Δx indicates spatial translation. This can be in any direction. However, cardinal directions are simplest for 2-D sensing arrays.

If there is a change signal from B(x−Δx) the determination is then made as to whether there is a change signal transmitted from unit B(x) at time t+Δt (step 720), where Δt indicates temporal translation.

If the product of the two change signals is greater than a predetermined threshold $G_{th}$, wherein $$G = B(x,t+\Delta t)*B(x-\Delta x,t) > G_{th}$$

Layer G will report detection of motion at pixel P(j,k) in direction Δx at time t+Δt (step 730).

The operation of Layer G can be illustrated with reference to the example array in FIG. 6.

Example #1

$B_{1,t}$=input from B(1,1) at time t
$B_{2,t+\Delta t}$=input from B(1,2) at time t+Δt
If $B_{1,t}*B_{2,t+\Delta t} > G_{th}$, $G_{1,2,1}$ will report rightwards motion at time t+Δt. The first subscript of $G_{1,2,1}$ indicates rightward motion, and the second and third subscripts indicate the pixel where motion will be reported.

Example #2

$B_{1,t}$=input from B(4,2) at time t
$B_{2,t+\Delta t}$=input from B(4,3) at time t+Δt
If $B_{1,t}*B_{2,t+\Delta t} > G_{th}$, $G_{2,4,3}$ will report downwards motion at time t+Δt, where the first subscript indicates downward motion, and the second and third subscripts indicate the pixel where motion will be reported.

The motion value determined in step 730 is sent to Layer L for size tuning. If Layer L determines that there is a large object of no interest (explained in more detail below) it will produce a suppressive signal that is applied to motion value G (step 740) to produce a modified motion value G', such that $$G'_{i,j,k} = G_{i,j,k} - L_{i,j,k}$$

where $L_{i,j,k}$ is value of the suppressive signal produced by Layer L.

This modified motion value G' may then be modified yet again if the global tuning unit in Layer A detects sensor jitter to produce new motion value G" (step 750), wherein $$G''_{i,j,k} = G'_{i,j,k} - A$$

where A is the value of the global motion suppressive signal from Layer A. The globally tuned motion value G" is then transmitted to the ground station or control station for processing (step 760).

Figure 9:
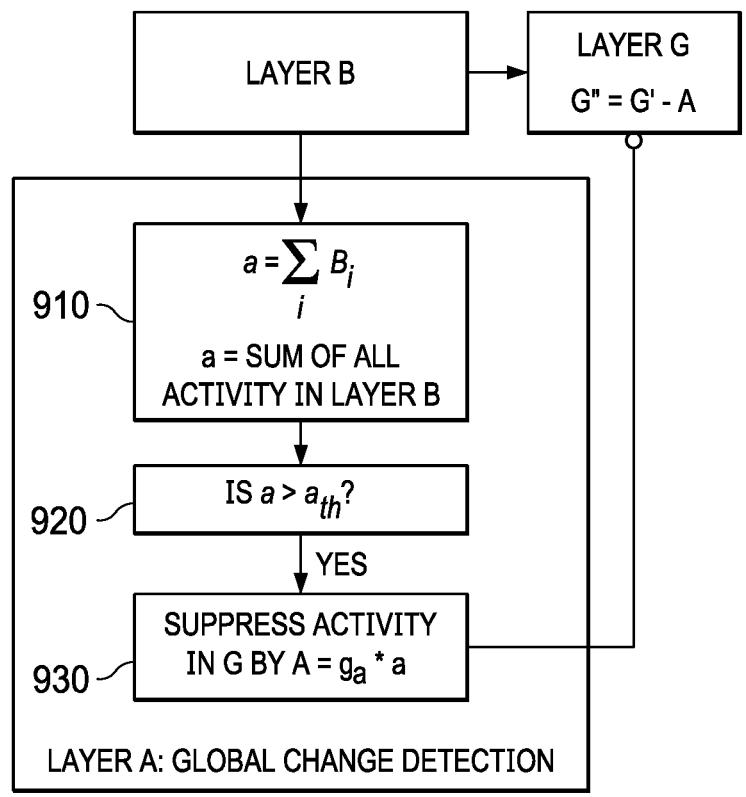
FIG. 9 depicts a process flow for detecting global change in pixel values and producing a suppressive signal in accordance with an illustrative embodiment.

FIG. 9 depicts a process flow for detecting global change in pixel values and producing a suppressive signal in accordance with an illustrative embodiment. After receiving the pixel value change signals from Layer B, the global tuning unit adds up the total activity in Layer B for the predetermined field of view to produce the sum $$a = \Sigma_i B_i$$

where a equals the sum of all activity in Layer B (step 910). The global tuner then determines if $a > a_{th}$, where $a_{th}$ is a predetermined threshold value (step 920).

If the value of a exceeds the threshold value $a_{th}$, a suppressive signal A is generated to modify the motion signal from Layer G (step 930), wherein $$A = g_a * a$$

where $g_a$ is a parameter determining the suppressive effect of A on units within layer G.

Figure 10:
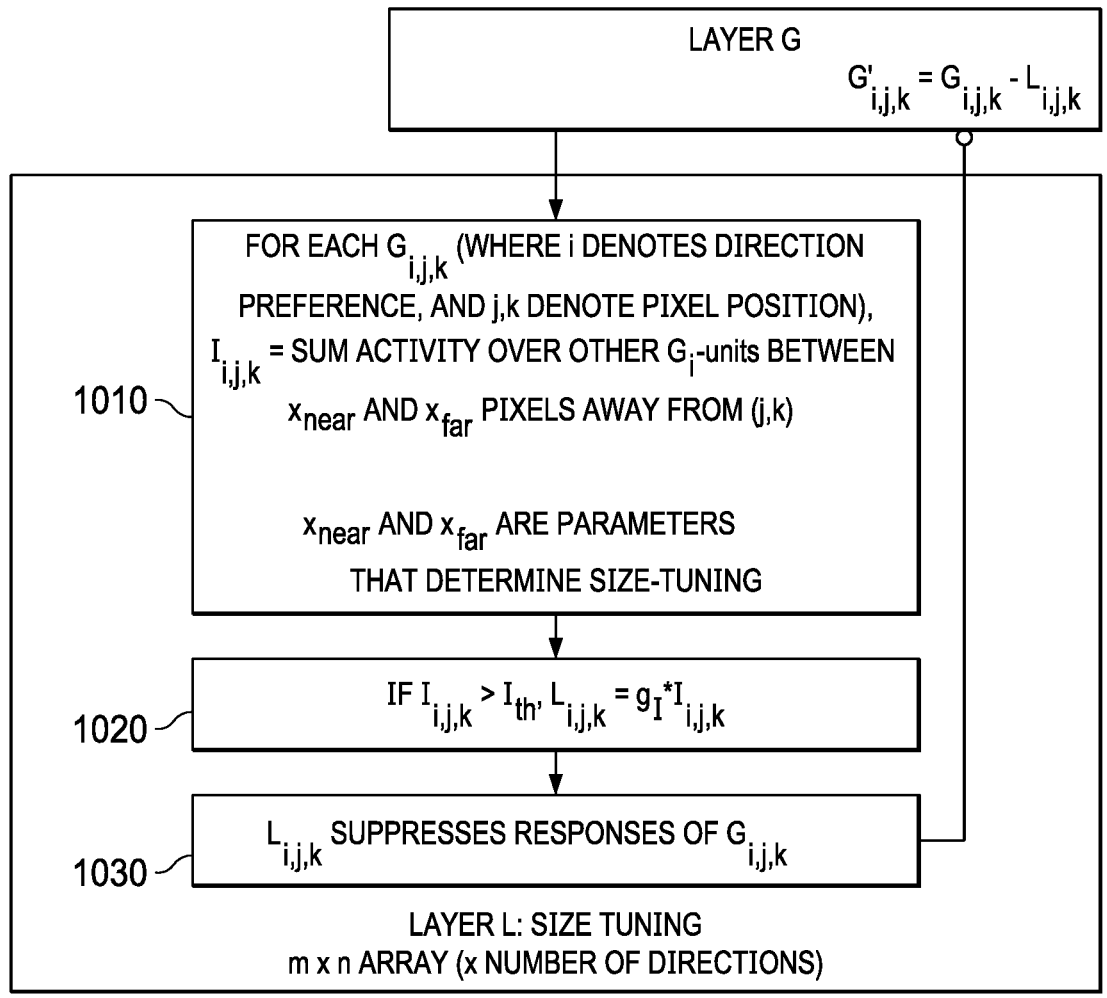
FIG. 10 depicts a process flow for tuning motion signals to account for large objects in accordance with an illustrative embodiment.

FIG. 10 depicts a process flow for tuning motion signals to account for large objects in accordance with an illustrative embodiment. For each unit $G_{i,j,k}$ the lateral tuning units in Layer L calculate a sum of activity $I_{i,j,k}$ over other $G_i$ units within a certain pixel distance from $G_{i,j,k}$ (step 1010), where the subscript i denotes direction preference, and j,k denote pixel position.

The $G_i$ units included in the sum $I_{i,j,k}$ are between $x_{near}$ and $x_{far}$ pixels away from (j,k), where $x_{near}$ and $x_{far}$ are predetermined parameters for defining subsections within the sensor's field of view.

If $I_{i,j,k}$ is greater than a predetermined threshold value $I_{th}$ a suppressive signal value $L_{i,j,k}$ is generated (step 1020), wherein $$L_{i,j,k} = G_I * I_{i,j,k}$$

where $g_I$ is a parameter determining the suppressive effect of $L_{i,j,k}$ on $G_{i,j,k}$.

This signal $L_{i,j,k}$ suppresses the response of $G_{i,j,k}$ in Layer G (step 1030).

FIG. 11 depicts an example application of size tuning to an array of motion detection units in Layer G in accordance with an illustrative embodiment. In this example, the center unit $G_{(3,3)}$ is the one of interest. For ease of illustration in this example $x_{near} = x_{far} = 2$. This means that the activity of pixels that are two pixel positions from (3,3) (the outer most positions around the array shown in FIG. 11) are summed such that $$I_{i,3,3} = G_{i,1,1} + G_{i,1,2} + G_{i,1,3} + G_{i,1,4} + G_{i,1,5} + G_{i,2,5} + G_{i,3,5} + G_{i,4,5} + G_{i,5,5} + G_{i,5,4} + G_{i,5,3} + G_{i,5,2} + G_{i,5,1} + G_{i,4,1} + G_{i,3,1} + G_{i,2,1}$$

If $I_{i,3,3} > I_{th}$ Layer L generates a signal $L_{i,3,3}$ that is a suppressive input to $G_{i,3,3}$.

The present disclosure is applicable to detecting small moving objects such as vehicles or people on ground, airborne targets presented against earth background, and moving targets in the air or earth's orbit.

Layers B, G, A, and L can be implement in whole or in part on a field programmable gate array (FPGA) or custom-designed/programmed neuromorphic hardware.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A sensor data preprocessing device, comprising:
   a first layer of detectors configured to receive signals from an array of sensor pixels and determine changes in pixel values;
   a second layer of detectors configured to receive the changes in pixel values from the first layer, detect motion based on the changes in pixel values and transmit motion value output signals to a processing station;
   a third layer of detectors configured to receive the changes in pixel values from the first layer and detect global motion of objects represented by correlated changes in pixel values across a predetermined field of view, wherein the third layer is configured to produce a first suppressive signal that is applied to the motion value output signals of the second layer of detectors only if a sum of correlated changes in pixel values within the predetermined field of view exceeds a predetermined threshold; and
   a fourth layer of detectors configured to receive motion output signals from the second layer and detect large environmental objects by integrating motion values within defined subsections of the predetermined field of view, wherein the fourth layer is configured to produce a second suppressive signal that is applied to the motion value output signals of detectors in the second layer for a subsection only if a sum of motion values within that subsection exceeds a predetermined threshold.

2. The device according to claim 1, wherein the device is incorporated into a remote sensor.

3. The device according to claim 2, wherein the remote sensor is selected from among the following:
   a camera;
   an unmanned aerial vehicle (UAV);
   telescope;
   satellite.

4. The device according to claim 1, wherein the first layer is configured to transmit only positive changes in pixel values to the second layer.

5. The device according to claim 1, wherein the first layer is configured to transmit only negative changes in pixel values to the second layer.

6. The device according to claim 1, wherein the first layer is configured to transmit both positive and negative changes in pixel values to the second layer.

7. The device according to claim 1, wherein the second layer is configured to detect motion across two pixels.

8. The device according to claim 1, wherein the sum of correlated changes in pixel values across the field of view exceeding the predetermined threshold indicates sensor jitter.

9. The device according to claim 1, wherein the sum of motion values within a subsection exceeding the predetermined threshold indicates the presence of an object larger than a predetermined size to be considered of interest.

10. The device according to claim 1, wherein subsections of the field of view are defined by predetermined distances between sensor pixels.

11. The device according to claim 1, wherein the device is implemented at least in part in neuromorphic hardware.

12. The device according to claim 1, wherein the device is implemented at least in part in a field programmable gate array (FPGA).

13. A method of preprocessing sensor data, comprising the steps of:
    receiving, by a first layer of detectors, signals from an array of sensor pixels;
    determining, by the first layer of detectors, changes in pixel values;
    detecting, by a second layer of detectors, motion based on the changes in pixel values;
    transmitting, by the second layer of detectors, motion value output signals to a processing station;
    detecting, by a third layer of detectors, global motion of objects represented by correlated changes in pixel values across a predetermined field of view;
    producing, by the third layer of detectors, a first suppressive signal that is applied to the motion value output signals of the second layer of detectors only if a sum of correlated changes in pixel values within the predetermined field of view exceeds a predetermined threshold;
    detecting, by a fourth layer of detectors, large environmental objects by integrating motion values within defined subsections of the predetermined field of view; and producing, by the fourth layer of detectors, a second suppressive signal that is applied to the motion value output signals of detectors in the second layer for a subsection only if a sum of motion values within that subsection exceeds a predetermined threshold.

14. The method according to claim 13, wherein only positive changes in pixel values are used to detect motion.

15. The method according to claim 13, wherein only negative changes in pixel values are used to detect motion.

16. The method according to claim 13, wherein both positive and negative changes in pixel values are used to detect motion.

17. The method according to claim 13, wherein change across two pixels indicates local motion.

18. The method according to claim 13, wherein the sum of correlated changes in pixel values across the field of view exceeding the predetermined threshold indicates sensor jitter.

19. The method according to claim 13, wherein the sum of motion values within a subsection exceeds the predetermined threshold indicates the presence of an object larger than a predetermined size to be considered of interest.

20. The method according to claim 13, wherein subsections of the field of view are defined by predetermined distances between sensor pixels.

* * * * *